United States Patent
Nagai et al.

(10) Patent No.: US 6,694,747 B2
(45) Date of Patent: Feb. 24, 2004

(54) LIQUID CONTAINER AND AN ANALYZER EQUIPPED THEREWITH

(75) Inventors: Takaaki Nagai, Kobe (JP); Hiroaki Tobimatsu, Kobe (JP)

(73) Assignee: Sysmex Corporation (JP)

( * ) Notice: Subject to any disclaimer, the term of this patent is extended or adjusted under 35 U.S.C. 154(b) by 0 days.

(21) Appl. No.: 10/163,388

(22) Filed: Jun. 4, 2002

(65) Prior Publication Data

US 2003/0000225 A1 Jan. 2, 2003

(30) Foreign Application Priority Data

Jun. 7, 2001 (JP) .................................. 2001-172964

(51) Int. Cl.$^7$ ............................................... F25B 21/02
(52) U.S. Cl. ............................................. 62/3.3; 62/3.7
(58) Field of Search .......................... 62/3.7, 3.2, 3.3, 62/3.4

(56) References Cited

U.S. PATENT DOCUMENTS

| | | | |
|---|---|---|---|
| 4,494,380 A | * 1/1985 | Cross | .............................. 62/3 |
| 5,232,516 A | * 8/1993 | Hed | ............................. 136/204 |
| 5,387,334 A | 2/1995 | Kuroda et al. | |
| 5,679,575 A | 10/1997 | Kubota et al. | |
| 5,737,923 A | * 4/1998 | Gilley et al. | ................... 62/3.7 |
| 5,761,909 A | * 6/1998 | Hughes et al. | ................ 62/3.7 |
| 5,802,856 A | * 9/1998 | Schaper et al. | ............... 62/3.7 |
| 5,822,993 A | * 10/1998 | Attey | ............................ 62/3.7 |
| 6,226,994 B1 | * 5/2001 | Yamada et al. | ............... 62/3.7 |
| 6,446,442 B1 | * 9/2002 | Batchelor et al. | ............. 62/3.3 |

* cited by examiner

*Primary Examiner*—Melvin Jones
(74) *Attorney, Agent, or Firm*—Brinks Hofer Gilson & Lione

(57) ABSTRACT

A liquid container comprising a base having openings that communicate from the front surface to the back surface, and first and second sealing plates that seal the openings from both sides of the base to form internal spaces, wherein the sealing plates comprise a first heat exchanging member for heating or cooling the internal space from the front surface of the base and a second heat exchanging member for heating or cooling the internal space from the back surface of the base.

20 Claims, 4 Drawing Sheets

LIQUID CONTAINER AND AN ANALYZER EQUIPPED THEREWITH

BACKGROUND

The present invention relates to a liquid container used for heating or cooling a liquid contained inside the container, for example, a liquid heater/cooler built into a sample analyzer for heating, cooling or maintaining the temperature of a dilution or liquid reagent in order to maintain the dilution or reaction condition at a constant level.

A liquid heater of this kind has been known, in which a cylindrical container is provided inside a cubical block made of stainless steel or ceramic for accommodating liquid. A heater provided on each of the two opposing surfaces of the block is employed to heat the liquid in the container, while a mechanism for guiding the liquid close to the side wall of the container and a mechanism to separate the heated liquid from the unheated liquid are provided inside the container for the purpose of controlling heat conductance to the liquid (e.g., U.S. Pat. No. 5,387,334).

SUMMARY

The present invention provides a liquid container which, compared with conventional liquid containers, has a higher heat exchange ratio and a simpler configuration so that it is easier to manufacture.

In one embodiment, the invention provides a liquid container comprising a base having openings that communicate from the front surface to the back surface, and first and second sealing plates that seal the openings from both sides of the base to form internal spaces, wherein the sealing plates comprise a first heat exchanging member for heating or cooling the internal space from the front surface of the base and a second heat exchanging member for heating or cooling the internal space from the back surface of the base.

Since the liquid container of this embodiment has a base having an opening as well as first and second sealing plates as the basic elements of its configuration, the constitution is simpler and easier to manufacture.

In another embodiment, the invention provides a liquid container comprising a base having openings that communicate from the front surface to the back surface, first and second sealing plates that seal the openings from both sides of the base to form internal spaces, and an electric power supply circuit to supply electric power to heat or cool a liquid in the internal space, wherein the sealing plates comprise a first Peltier element that supplies heat to the internal space and absorbs heat from the internal space through the front surface of the base and a second Peltier element that supplies heat to the internal space and absorbs heat from the internal space through the back surface of the base; and the electric power circuit is capable of reversing the flow direction of the current supplied to the first and second Peltier elements.

DESCRIPTION OF THE PRESENTLY PREFERRED EMBODIMENTS

The present invention will be described in detail referring to the embodiments shown in the accompanying drawings. This description should not be considered to limit the invention in any way.

Figure 1:
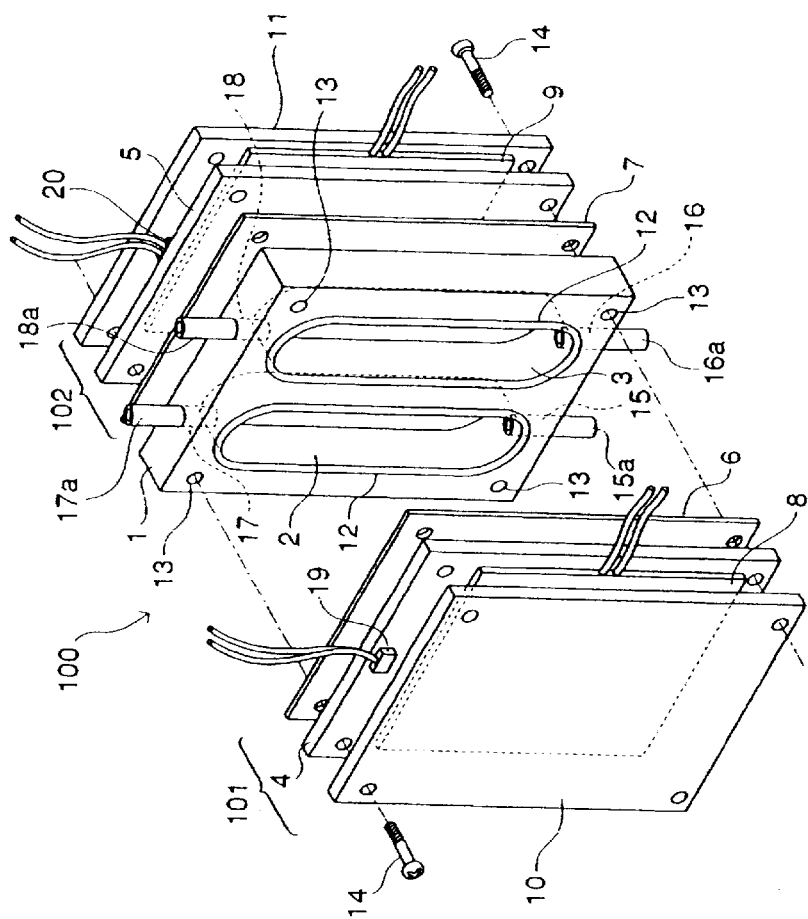
FIG. 1 An exploded perspective view showing a liquid heater according to an embodiment of the present invention.

FIG. 1 is an exploded perspective view showing a liquid heater according to an embodiment of the present invention. As shown in this drawing, a main unit 100 comprises a base 1, and first and second sealing plates 101 and 102. Base 1 has two openings 2 and 3 that communicate from the front surface to the back surface.

Since the liquid heater of this embodiment is used for heating reagent, the base 1 and first and second sealing plates 101 and 102 preferably have chemical resistance. Base 1 is preferably made of metals, plastics, or ceramics with excellent chemical resistance. For example, it is preferably made of stainless steel in the case of metals, and polyetherimide, polyetherketone or polyacetal in the case of plastics.

If it is made of plastics, base 1 can be mass-produced with high precision using a forming process such as injection molding.

First sealing plate 101 comprises a first heat conductive plate 4, a plastic film 6, a film-like heater 8 and a heat insulation plate 10. Second sealing plate 102 comprises a second heat conductive plate 5, a plastic film 7, a film-like heater 9 and a heat insulation plate 11.

A material suitable for heat conductive plates 4 and 5 can be a metal with a high heat conductivity, such as aluminum, copper, and silver (however, the chemical resistance of these metals is low).

Although it is preferable for heat insulation plate 11 to cover main unit 100 entirely, the heat insulation plate can curb unnecessary heat leakage or consumption of the heater by covering at least a portion of film-like heaters 8 and 9.

Film-like heaters 8 and 9 are adhered to the back of first and second heat conductive plates 4 and 5, respectively, with silicon adhesives. First and second heat conductive plates 4 and 5 seal openings 2 and 3 on both sides of base 1 via plastic films 6 and 7, and conduct heat from heaters 8 and 9 to openings 2 and 3, respectively.

Silicon rubber heaters can be used as film-like heaters 8 and 9. It is also possible to replace film-like heaters 8 and 9 with Peltier elements.

It is possible to use fluoric resin film for plastic films 6 and 7. The thickness of the films is preferably as thin as possible from the standpoint of heat conductivity, but is preferably 0.1–0.5 mm from the standpoint of mechanical strength.

Insulation plates 10 and 11 are further installed behind heaters 8 and 9, respectively. O-rings 12 are installed on annular grooves (not shown) provided to encircle openings 2 and 3 on both the front and back surfaces of base 1 (two O-rings on each surface, i.e., four O-rings in total) and a tapped through hole 13 is provided on each corner of base 1.

During the assembly process, heat insulation plate 10, first heat conductive plate 4, and plastic film 6 are affixed to the surface of base 1 by means of four screws 14 that can engage with tapped through holes 13. Similarly, heat insulation plate 11, heat conductive plate 5, and plastic film 7 are affixed to the back of base 1 by means of four screws 14 that can engage with tapped through holes 13.

Thus, first and second heat conductive plates 4 and 5 seal openings 2 and 3 completely via plastic films 6 and 7 to form two internal spaces.

Liquid supply ports 15 and 16 communicating from the bottom surface to openings 2 and 3 are provided on base 1, and nipples 15a and 16a are provided on liquid supply ports 15 and 16, respectively, for connecting reagent supply tubes.

Liquid discharge ports 17 and 18 communicating from the top surface to openings 2 and 3 are provided on base 1, and nipples 17a and 18a are provided on liquid supply ports 17 and 18, respectively, for connecting reagent discharge tubes.

By providing liquid supply ports on the bottom surface and liquid discharge ports on the top surface as shown above, it is possible to prevent bubble generation in the internal space when supplying liquid into the internal space.

Temperature sensors 19 and 20 are provided on heat conductive plates 4 and 5, respectively.

The volume V of the internal space of the liquid heater according to this embodiment is determined essentially by a product of the opening area S and the base thickness T, i.e., the relationship $V=ST$ holds.

In the liquid heater of this embodiment, when a liquid with volume V is stored in the internal space, film-like heaters 8 and 9 heat the liquid from the entire surface of both sides of the opening having area S.

Therefore, if the volume V is constant, it is possible to have an extremely high heat exchange rate for the liquid by increasing the opening area S and reducing the thickness T.

Base 1 is a polyetherimide plate with a thickness $T=6$ mm, while plastic films 6 and 7 are fluoric resin films with thicknesses of 0.2 mm, which are adhered to surfaces of heat conductive plates 4 and 5 in advance. Heat conductive plates 4 and 5 are aluminum plates with a thickness of 3.0 mm. Heat insulation plates 10 and 11 are made of foaming polyethylene. Openings 2 and 3 have a circumference length L of 13 cm and an area S of 10 $cm^2$, respectively, and the internal spaces formed by openings 2 and 3, respectively, have a volume V of 6 mL.

Therefore, when 6 mL of liquid is supplied to the two internal spaces of main unit 100 via nipples 15a and 16a, respectively, and electricity is supplied to film-like heaters 8 and 9, heat is supplied from film-like heaters 8 and 9 to liquid, through heat conductive plates 4 and 5 as well as plastic films 6 and 7. At this time, the liquid contained in each internal space of openings 2 and 3 is surrounded by walls with a surface area of 27.8 cm 2 (L×T+2S), and receives heat from the heaters 8 and 9 through a wall area 20 $cm^2$ (2×S), i.e., 72% of all wall areas (2S×100/(L×T+2S)). Therefore, the heat of film-like heaters 8 and 9 are transmitted very efficiently to the liquid, providing a high heat exchange ratio.

Figure 2:
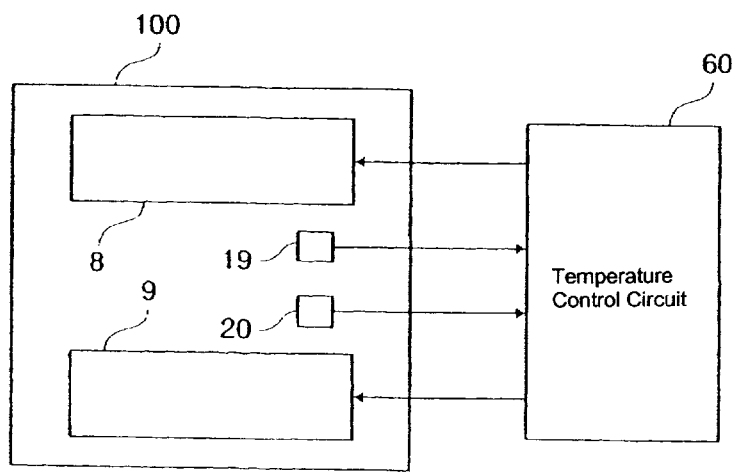
FIG. 2 An electrical circuit diagram for controlling an embodiment of the present invention.

FIG. 2 is an electrical circuit diagram for controlling a liquid heater according to the present invention. Film-like heaters 8 and 9 as well as temperature sensors 19 and 20 are connected to temperature control circuit 60. Temperature control circuit 60 controls the status of electric power supply to film-like heaters 8 and 9 based on temperature information obtained from temperature sensors 19 and 20 in order to control the temperature of the liquid contained in main unit 100 to the desired temperature. In this case, for example, the control circuit 60 sets the liquid temperature at 47±2° C. Well-known technology can be used for the temperature control circuit as shown in FIG. 4.

Figure 4:
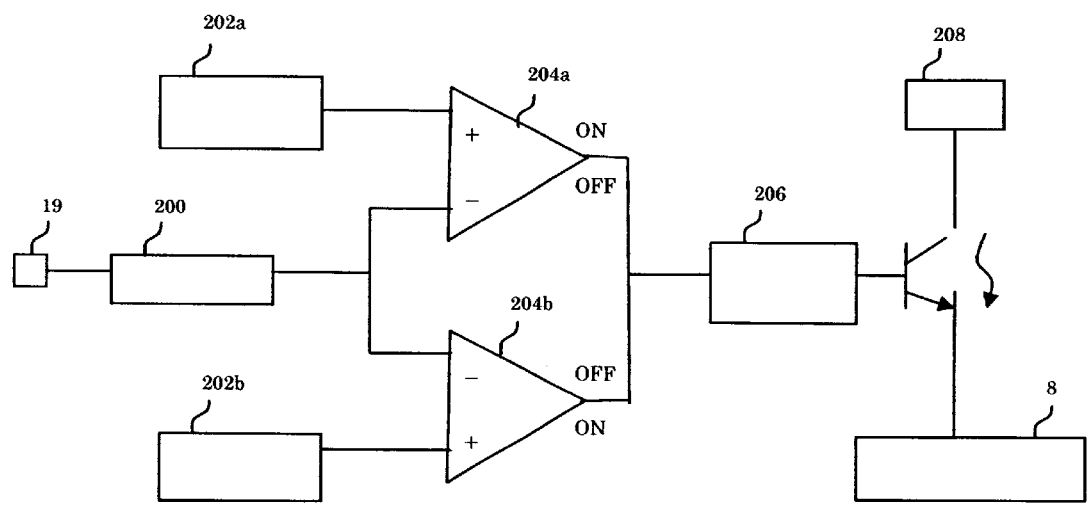
FIG. 4 An electrical circuit diagram for showing an embodiment of the temperature control circuit.

Let us briefly describe the temperature control circuit shown in FIG. 4. The temperature information issued from temperature sensor 19 is converted into voltage by a voltage conversion circuit 200. The voltage is compared with the voltages generated by a target voltage (low) generating circuit 202a and a target voltage (high) generating circuit 202b at comparators 204a and 204b, and the results of comparisons are processed by a logic circuit 206 to be used for controlling the power supply from power source 208 to film-like heater 8.

The liquid supplied to main unit 100 through nipples 15a and 16a is held in main unit 100 for a specified period of time to be discharged when it reaches the desired temperature. Such a temperature-controlled liquid includes diluting liquids for diluting blood samples and hemolytic liquids for hemolyzing red blood cells.

Liquid heater 100 can be built into an analyzer. Applicable analyzers include various analyzers for diluting liquids and reagents and other liquids such as sample analyzers including blood analyzers and urine analyzers or industrial particle analyzers. A case where liquid heater 100 is built into a blood analyzer is described below.

Figure 3:
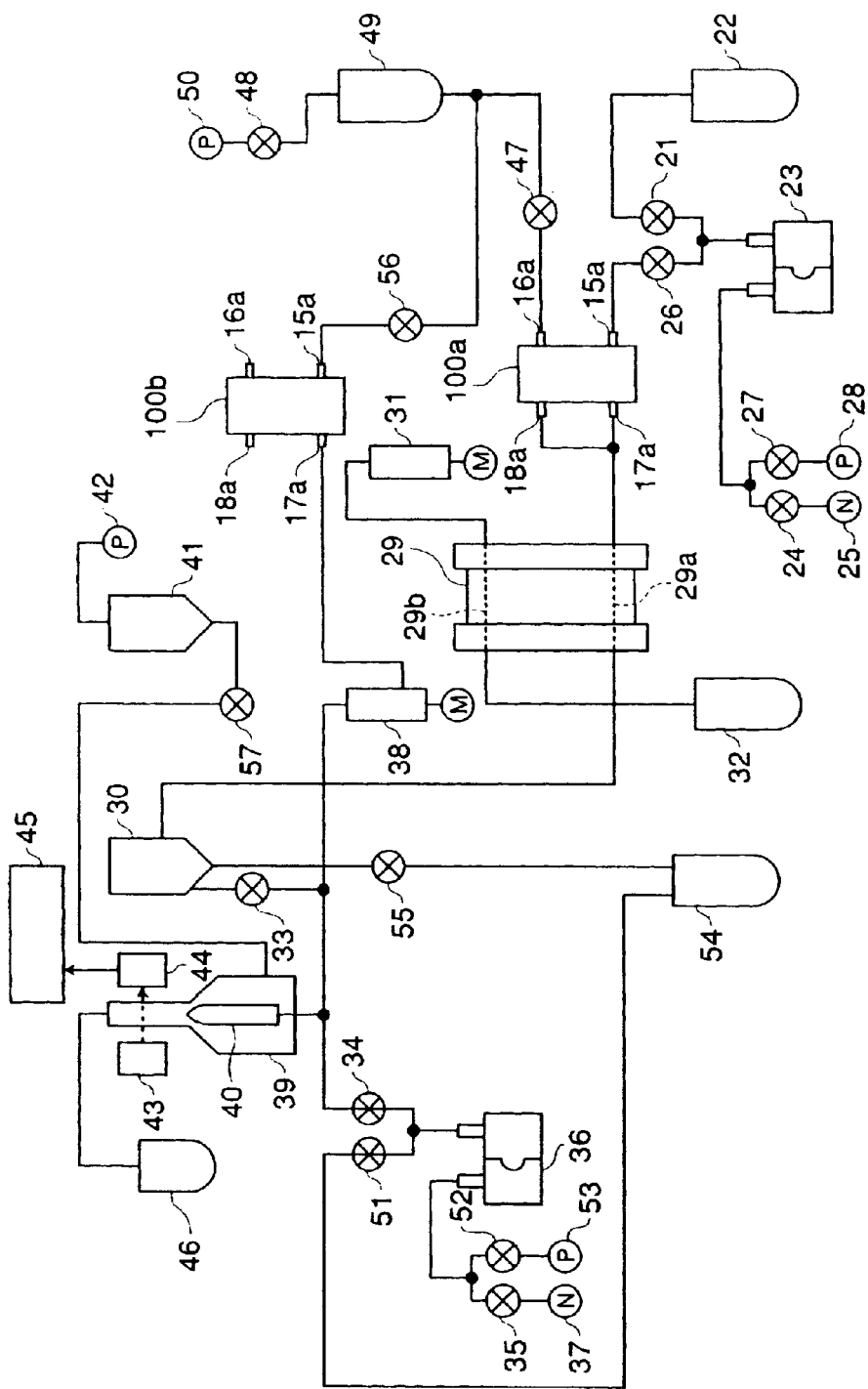
FIG. 3 A diagram for describing the configuration of a blood analyzer using the liquid heaters shown in FIG. 1.

FIG. 3 is a diagram for describing the configuration of a blood analyzer using a flow cytometer and two liquid heaters shown in FIG. 1 and FIG. 2. A blood analyzer using a flow cytometer is described, for example, in U.S. Pat. No. 5,679,575.

Let us briefly describe the configuration of the blood analyzer shown in FIG. 3. This blood analyzer comprises valves 21, 24, 26, 27, 33, 34, 35, 47, 48, 51, 52, 55, 56, and 57 for opening/closing flow passages, negative pressures 25 and 37 that supply negative pressure to the flow passages, positive pressures 28, 42, 50, and 53 that supply positive pressure to the flow passages, a sampling valve 29 for measuring liquids, diaphragm pumps 23 and 36 for sucking and discharging specified amounts of liquids, chambers 22, 30, 32, 41, 46, 49, and 54 for holding various liquids, a sheath flow cell 39 for allowing diluted samples to pass, syringes 31 and 38 for allowing specific amounts of fluid to be transferred, and liquid heaters 100a and 100b shown in FIG. 1 and FIG. 2, wherein tubing to connect these parts is conducted to form passages. This blood analyzer also includes light-emitting element 43 that irradiates sheath flow cell 39 with light, a light-receiving element 44 for detecting lights such as scattered lights and fluorescent lights emitted from particles contained in a diluted sample, and an analyzing unit 45 for analyzing characteristics of the particles in the diluted sample based on detection results by the light-receiving element 44.

Although we identify two liquid heaters separately as 100a and 100b for the sake of description, both units are identical to the above-described liquid heater main unit 100.

In FIG. 3, valve 21 is opened first to allow reagent chamber 22 to communicate with diaphragm pump 23. Next, valve 24 is opened to allow, by means of negative pressure 25, 1 mL of a reagent (diluting liquid) to be sucked into diaphragm pump 23. When valves 21 and 24 are closed and valves 26 and 27 are opened, by means of positive pressure 28, 1 mL of the reagent is fed into liquid heater main unit 100a from diaphragm pump 23 through nipple 15a. Next, valves 26 and 27 are closed. The reagent supplied to liquid heater 100a is then heated inside the internal spaces.

By repeating the operations from the opening of valve 21 through the closing of valves 26 and 27 several times, the reagent heated to the specified temperature is sent out through nipple 17a to fill the passage up to reaction chamber 30 via reagent passage 29a of sampling valve 29.

Next, syringe 31 is operated to suck the sample (blood) from sample chamber 32 into measuring passage 29b of sampling valve 29. The sample (4 μL) is quantified by rotating sampling valve 29, which switches measuring passage 29b to reagent passage 29a. This makes the sample sandwiched between the two segments of reagent. Next, when 1 mL of reagent is transferred from main unit 100a by operating diaphragm pump 23 as described above, 4 μL of the sample flows into reaction chamber 30 together with 1 mL of reagent and is agitated in reaction chamber 30 to produce a diluted sample.

Next, valves 33, 34, and 35 are opened to apply negative pressure 37 to diaphragm pump 36. The passage between reaction chamber 30 and valve 34 becomes filled with the diluted sample. Valves 33 and 34 are closed and syringe 38 is operated. Then the diluted sample is discharged from nozzle 40 inside sheath flow cell 39.

Alternatively, when valve 57 is opened, the sheath liquid is fed from chamber 41 to sheath flow cell 39 by means of positive pressure 42, and the diluted sample discharged from nozzle 40 is enveloped to form a so-called sheath flow. This sheath flow is then irradiated with light by light-emitting element 43, thus causing scattered light and fluorescent light generated by particles contained in the diluted sample to be detected by light-receiving element 44.

Analyzing unit 45 analyzes the characteristics of the particles contained in the diluted sample based on detected light intensities. The diluted sample and the sheath liquid that constitute the sheath flow are then discharged into discharge liquid chamber 46.

When the analysis operation is completed as described above, the wash operation is performed next.

First, valves 47 and 48 are opened. Positive pressure 50 is applied to wash liquid chamber 49 causing the wash liquid to flow through valve 47, nipple 16a, main unit 100a, nipple 18a, sampling valve 29, and reaction chamber 30. Valves 47 and 48 are closed before reaction chamber 30 becomes saturated.

Valves 33, 34, and 35 are opened to apply negative pressure 37 to diaphragm pump 36 in order to suck the wash liquid from reaction chamber 30 to diaphragm pump 36 through valves 33 and 34. When valves 34 and 35 are closed, and valves 51 and 52 are opened to apply positive pressure 53 to diaphragm pump 36, the wash liquid in diaphragm pump 36 is discharged to discharge chamber 54 through valve 51. Next, when valve 55 is opened, the remaining wash liquid in reaction chamber 30 is discharged to discharge chamber 54.

Next, when valves 48 and 56 are opened to apply positive pressure 50 to wash liquid chamber 49, the wash liquid is discharged to discharge chamber 46 from wash liquid chamber 49 through valve 56, liquid heater main unit 100b, syringe 38, nozzle 40 and sheath flow cell 39. Thus, the wash operation is completed. The wash liquid is heated by the liquid heater similar to the reagent for preventing the wash liquid from cooling the passage.

Although film-like heaters are used as the heaters, the present invention is not limited to this configuration. For example, it is possible to provide a liquid cooler to cool the liquid contained in the space by use of a Peltier element in place of a film-like heater whose cooling surface faces base 1. In this case, it is preferable not to use insulating plates 10 and 11 to radiate heat.

When using a Peltier element, it is possible to provide a liquid heater/cooler, which can be used to heat or cool the liquid by providing a current switching circuit, which enables the direction of the electric current supplied to the Peltier element to be changed.

Figure 5:
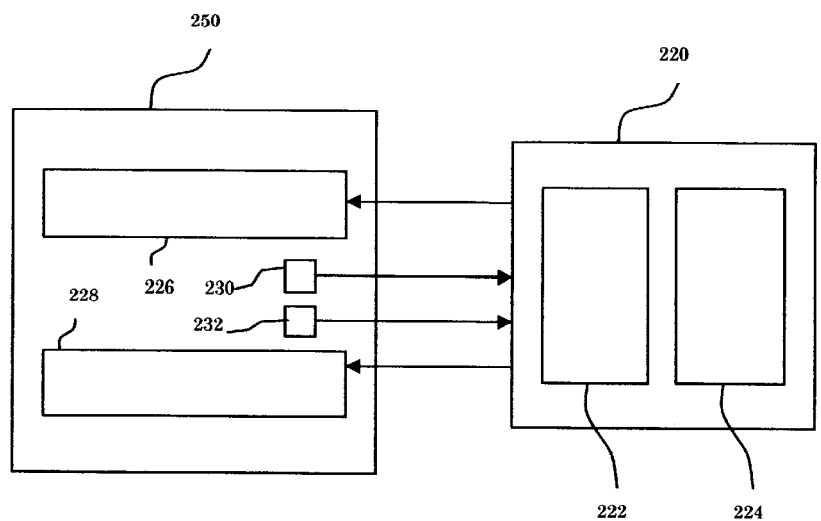
FIG. 5 An electrical circuit diagram for controlling an embodiment of a liquid heater/cooler.
Figure 6:
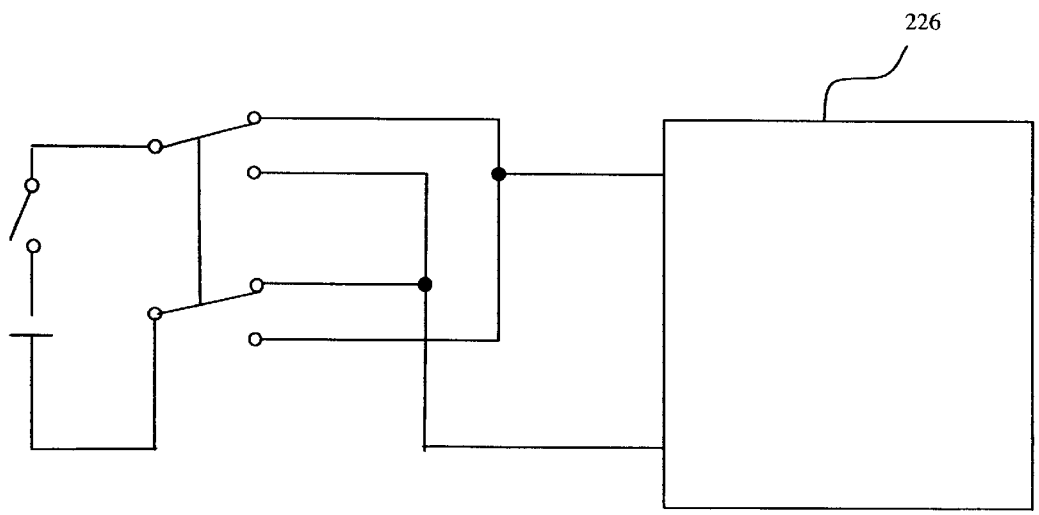
FIG. 6 A current switching circuit used for the electrical circuit shown in FIG. 5.

FIG. 5 shows an electrical circuit diagram for controlling an embodiment of a liquid heater/cooler. A liquid heater/cooler 250 is equipped with Peltier elements 226 and 228 as well as temperature sensors 230 and 232, and is connected to a heating/cooling switching circuit 220. Heating/cooling switching circuit 220 can be composed of a temperature control circuit 224 and a current switching circuit 222 as shown in FIG. 4. Current switching circuit 222 can be a circuit as exemplified in FIG. 6

What is claimed is:

1. A liquid container, comprising:
   a base having an opening that communicates from a front surface to a back surface; and
   first and second sealing plates that seal the opening from both sides of the base to form an internal space; wherein
   the first and sealing plate comprises a first heat exchanging member for heating or cooling the internal space from the front surface of the base; and
   the second sealing plate comprises a second heat exchanging member for heating or cooling the internal space from the back surface of the base.

2. The liquid container of claim 1, wherein said base comprises a supply port for supplying liquid to the internal space and a discharge port for discharging liquid from the internal space.

3. The liquid container of claim 2, wherein said supply port comprises a first communicating hole communicating from the internal space to a first end of the base, and said discharge port comprises a second communicating hole communicating from the internal space to a second end of the base.

4. The liquid container of claim 3, wherein the first communicating hole is located on a bottom surface of the base and the second communicating hole is located on a top surface of the base.

5. The liquid container of claim 3, wherein the first and second communicating holes comprise nipples.

6. The liquid container of claim 2, wherein said opening comprises multiple openings each of which comprises a supply port and a discharge port.

7. The liquid container of claim 6, wherein the first sealing plate seals the multiple openings.

8. The liquid container of claim 1, wherein the first sealing plate comprises a heat conductive plate and the first heat-exchanging member comprises a film-like heater.

9. The liquid heater of claim 1, wherein said base comprises a chemical resistant material.

10. The liquid container of claim 1, wherein each the first sealing plate comprises a chemical resistant film, and the film is installed on the base.

11. The liquid container of claim 1, further comprising a packing member installed between the base and the first sealing plate.

12. The liquid container of claim 1, wherein the first sealing plate comprises a heat insulation member that covers at least a portion of the first heat-exchanging member.

13. An analyzer equipped-with comprising the liquid container of claim 1.

14. The analyzer of claim 13 further comprising:
   a temperature sensor for detecting a temperature of the first sealing plate; and
   a control circuit for controlling operation of the first and heat exchanging member based on the temperature detected by the temperature sensor.

15. The liquid container of claim 1, wherein said first and second heat-exchanging members are heating members that heat the internal space.

16. The liquid container of claim 1, wherein said first and second heat-exchanging members are cooling members that cool the internal space.

17. An analyzer, comprising:

a liquid container comprising a base having an opening that communicates from a front surface to a back surface; and
first and second sealing plates that seal the opening from both sides of the base to form an internal space; and an electric power supply circuit for supplying electric power for heating and cooling a liquid contained in the internal space, wherein the first sealing plates plate comprises:

a first Peltier element for supplying heat to the internal space and absorbing heat from the internal space via the front surface of the base; and the second sealing plate comprises a second Peltier element for supplying heat to the internal space and absorbing heat from the internal space via the back surface of the base; and the electric power supply circuit changes the direction of current being supplied to the first and second Peltier element.

18. The analyzer of claim 17, wherein said base comprises a supply port for supplying liquid to the internal space and a discharge port for discharging liquid from the internal space.

19. The analyzer of claim 18, wherein said opening comprises multiple openings each of which comprises a supply port and a discharge port.

20. The analyzer of claim 17, wherein the first sealing plate comprises a chemical resistant film, and the film is installed on the base.

* * * * *

UNITED STATES PATENT AND TRADEMARK OFFICE
CERTIFICATE OF CORRECTION

PATENT NO. : 6,694,747 B2
DATED : February 24, 2004
INVENTOR(S) : Takaaki Nagai et al.

It is certified that error appears in the above-identified patent and that said Letters Patent is hereby corrected as shown below:

Column 6,
Line 51, after "wherein" delete "each".
Line 60, delete "equipped-with".
Line 62, immediately after "claim 13" insert -- , -- (comma).
Line 65, after "the first" delete "and".

Column 7,
Line 16, after "internal space, wherein" start a new paragraph with the words "the first sealing".
Line 16, after "sealing" delete "plates".

Signed and Sealed this

Twenty-eighth Day of December, 2004

JON W. DUDAS
*Director of the United States Patent and Trademark Office*